United States Patent [19]

Hall

[11] Patent Number: 4,597,876

[45] Date of Patent: Jul. 1, 1986

[54] REGASIFYING PASTEURIZATION SYSTEM

[75] Inventor: Mark N. Hall, College Place, Wash.

[73] Assignee: Hallsonic Corporation, College Place, Wash.

[21] Appl. No.: 522,637

[22] Filed: Aug. 11, 1983

[51] Int. Cl.[4] .............................. C02F 1/20; C02F 1/36
[52] U.S. Cl. ..................................... 210/748; 210/750; 210/764; 55/48; 422/20
[58] Field of Search .................... 210/748, 750, 764; 422/20, 128; 55/48

[56] References Cited

U.S. PATENT DOCUMENTS

| | | | |
|---|---|---|---|
| 2,091,267 | 8/1937 | Chambers | 426/238 |
| 2,096,011 | 10/1937 | Smith | 426/238 |
| 2,109,912 | 3/1938 | Smith | 426/238 |
| 2,138,051 | 11/1938 | Williams | 366/113 |
| 2,138,052 | 11/1938 | Williams | 366/118 |
| 2,138,839 | 12/1938 | Chambers | 426/238 |
| 2,417,722 | 3/1947 | Wolff | 210/748 |
| 2,448,372 | 8/1948 | Horsley | 366/108 |
| 2,510,796 | 6/1950 | Brown | 99/451 |
| 2,693,944 | 11/1954 | Fowle | 366/116 |
| 3,087,840 | 4/1963 | Shaw | 366/108 |
| 3,212,756 | 10/1965 | Hutton | 366/116 |
| 3,294,063 | 12/1966 | Brodrick | 426/2 |
| 3,582,365 | 6/1971 | Lindsey | 426/238 |
| 3,617,178 | 11/1971 | Clouston | 422/22 |
| 3,672,823 | 6/1972 | Boucher | 422/20 |
| 3,676,983 | 7/1972 | Nold | 422/128 X |
| 3,686,115 | 8/1972 | Farman et al. | 210/748 |
| 4,086,057 | 4/1978 | Everett | 210/748 X |
| 4,145,450 | 3/1979 | Winder et al. | 426/231 |
| 4,193,818 | 3/1980 | Young et al. | 422/128 X |
| 4,211,744 | 7/1980 | Boucher | 422/20 |
| 4,428,757 | 1/1984 | Hall | 210/748 X |

OTHER PUBLICATIONS

Rectified Diffusion during Nonlinear Pulsations of Cavitation Bubbles—Ellelr—Flynn—1965.
Growth of Bubbles by Rectified Diffusion—Eller—1969.
Effects of Diffusion on Gaseous Cavitation Bubbles—Eller—1975.
Nonlinear Oscillations of Gas Bubbles in Liquids: Transient Solutions and the Connection Between Subharmonic Signal and Cavitation—Prosperetti—1975.
Numerical Investigation of Nonlinear Oscillations of Gas Bubbles in Liquids—Lauterborn—1976.
Measurements of the Growth of Air Bubbles by Rectified Diffusion—Crum—1980.
New Methods in Ultrasonic Processing—Alliger—1980.
Ultrasonic Disruption—Alliger—1975.

Primary Examiner—Thomas Wyse
Attorney, Agent, or Firm—Wells, St. John & Roberts

[57] ABSTRACT

Disclosed is a regasifying pasteurization system and related methods using compressional waves. The system first degasifies the incoming liquid acoustically and under a static pressure below atmospheric pressure. The compressional waves used in degasification are preferably modulated to increase efficiency. The degassed liquid is then exposed to vaporous cavitation in a microorganism disintegrator wherein microorganisms are disintegrated and killed, preferably using frequency modulated compressional waves and vacuum pressures. The regassified pasteurization system also includes a regasification subsystem which injects gases back into the liquid. The gases are sometimes the same gases removed during the degasification step. The degasification and disintegration step form independent subsystems and combine to form a pasteurization subsystem all of which can be used independent of the regasification subsystem.

19 Claims, 6 Drawing Figures

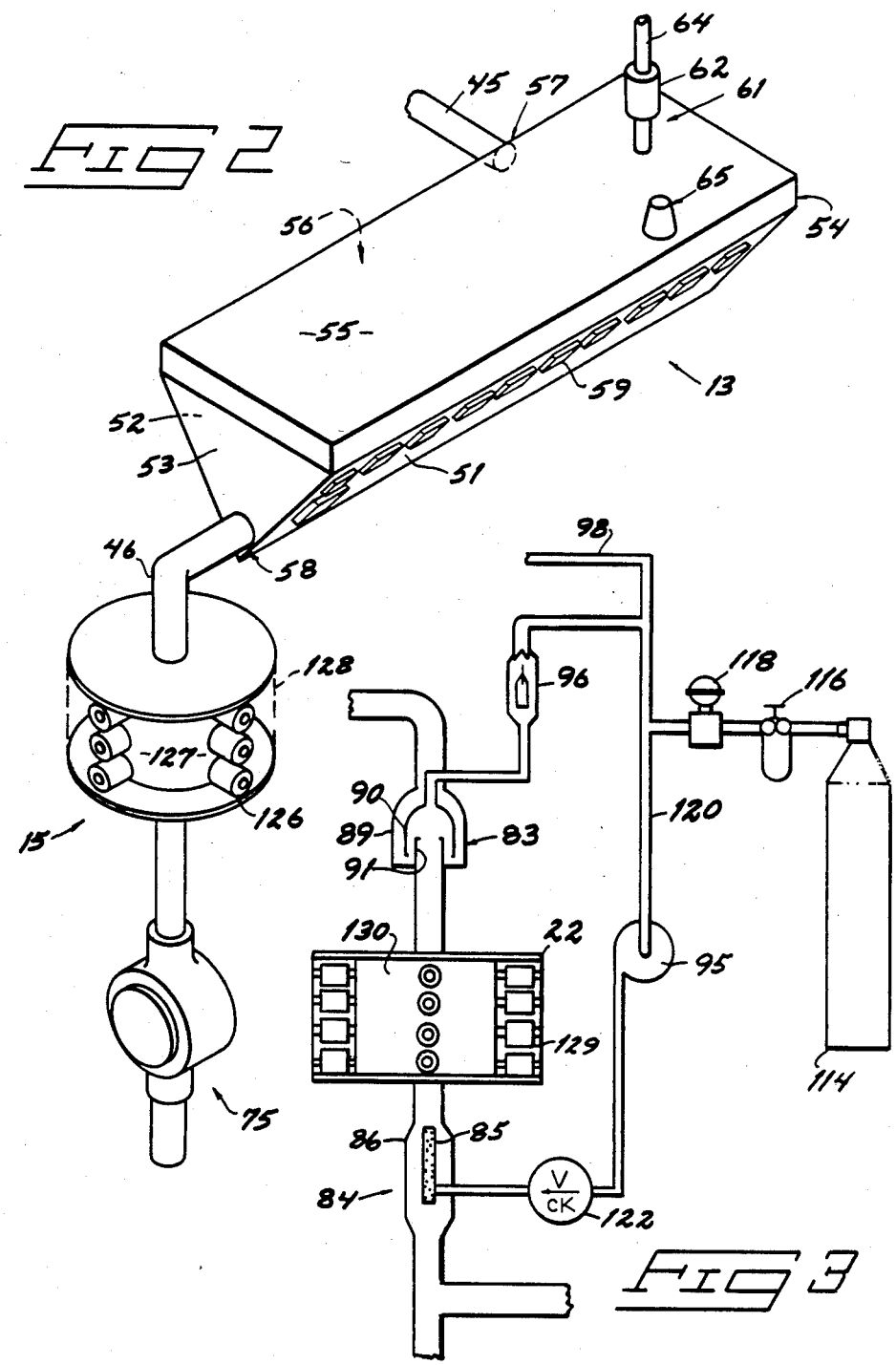

REGASIFYING PASTEURIZATION SYSTEM

TECHNICAL FIELD

The technical field of this invention is methods and apparatus for pasteurizing and gasifying liquids using sonic and ultrasonic compressional waves.

BACKGROUND OF THE INVENTION

The use of sonic and ultrasonic compressional waves to pasteurize liquids is well known in the art. Before considering the limitations and variations of prior art pasteurization methods, it is first advisable to consider the most widely recognized mechanism through which compressional waves destroy bacteria an other microorganisms.

U.S. Pat. No. 4,211,744 to Boucher explains that cavitation is the mechanism through which microorganisms are killed. Cavitation of a liquid using compressional waves involves the creation of small bubbles of vapor formed from the liquid involved. These small bubbles are formed in the decompression region behind the compressional wave front. As the magnitude of the pressure fluctuations in compressional waves increase, there is greater tendency for the liquid to vaporize into small bubbles. When the pressure front strikes these vapor bubbles, they implode. The implosion is believed to tear away small portions of the microorganisms or to physically break them into parts. Repeated cavitational attack tends to disintegrate the bacteria or other microorganisms thereby pasteurizing the liquid involved.

Prior art compressional wave pasteurization methods have used both sonic and ultrasonic frequencies. U.S. Pat. No. 2,138,839 to Chambers discloses a method using sonic compressional waves and static pressures of about 60 pounds per square inch or greater. Although Chambers recognizes the bacteriacidal action of cavitation, he explains that in his invention cavitation is not necessary to kill bacteria because of the application of relatively high static pressure. The high static pressure also prevents milk from homogenizing and keeps dissolved gases in beer.

U.S. Pat. No. 2,138,052 to Williams uses sonic frequency waves having very high acoustic pressure amplitudes, on the order of 10,000 atmospheres, to kill bacteria. The use of cavitation is avoided for the same reasons as explained above with regard to Chambers.

The invention shown in U.S. Pat. No. 2,417,722 to Wolff purifies liquids by subjecting them to either sonic or ultrasonic frequency compressional waves at acoustic pressure amplitudes of 100 to 200 bars. Wolff also bubbles oxygen gas through the liquid while subjecting it to these high pressure compressional waves. Wolff explains that the oxygen forms ozone which greatly accelerates the purification process.

U.S. Pat. No. 3,672,823 to Boucher explains that 100% kill rates are very difficult to obtain even using exposure times of 30 minutes or greater with acoustic power densities of several watts per cubic centimeter. Boucher addresses this problem by using ultraviolet radiation in combination with compressional waves.

U.S. Pat. No. 3,212,756 to Hutton discloses a sound generator which can produce compressional waves at more than one frequency and acoustic pressure amplitude. Hutton recognizes that certain frequencies are more effective or necessary to kill particular types of bacteria.

Sonic and ultrasonic pasteurization techniques have not been widely adopted in industry because of several limitations which render them economically unattractive. One problem is the large amount of acoustical power necessary to bring about pasteurization. In large scale processes this high power requirement requires a very large investment in compressional wave resonators. Even with very large systems, the treatment time is substantial in order to sufficiently kill microorganisms. The high flow rates of large scale continuous flow processes further aggravates the acoustic power and treatment time problems because of the reduced time available for treating the liquid. High acoustic power requirements also require that more expensive types of acoustic resonators and transducers be used to achieve the necessary power density.

Some prior art pasteurizers have decreased the pasteurization time and power requirements by combining heating with compressional wave treatment. Although this may be acceptable in many situations, there are many processes where heating the liquid affects the taste or chemistry in detrimental ways. Examples of products adversely affected include milk, beer and soft drinks. The taste of beer in particular is characterized by the natural carbonization which occurs in the brewing process. Heat and compressional waves both detrimentally affect the taste of beer and accordingly there has for a substantial number of years been a need for a heat free pasteurization system which does not detrimentally affect the taste.

Prior art compressional wave pasteurization systems failed to properly pasteurize beer because in general they removed the natural carbonization. The Williams and Chambers patents discussed above addressed this problem with high static pressure to keep the gases in the beer. The prior art failed to recognize that beer could be regasified with the same carbonization gases which were removed when the beer was exposed to compressional waves. The current invention provides for regasification using the gases removed during compressional wave pasteurization treatment.

Another limitation of prior art acoustic pasteurizers was their failure to recognize that pasteurization involves two distinct stages. The first stage of pasteurization is degassing the liquid to remove substantially all dissolved gases. Degassing occurs whenever a liquid is subjected to compressional waves of sufficient acoustic pressure amplitude. The action is sometimes described as "gaseous cavitation" or in some cases just "cavitation". Degassing is needed because the presence of dissolved gases prevents effective vaporous cavitation from occurring until substantially all dissolved gases are removed. Gaseous cavitation must be distinguished from vaporous cavitation because it is during vaporous cavitation that microorganisms are effectively and quickly killed.

Failure of the prior art to recognize this important phenomenon has resulted in one step pasteurization processes which do not efficiently or quickly degas the liquid because the primary design consideration was producing cavitation rather than efficient degassing. The current invention has discovered that much greater efficiency can be obtained by using different frequencies of compressional waves and different compression wave patterns for degassing than for vaporous cavitation. This two stage treatment reduces the time necessary to degas and reduces the time required to kill bacteria, spores and other microorganisms using vaporous cavitation. Thus the overall treatment time can be greatly reduced.

Another limitation of the prior art pasteurization units was their failure to recognize that the acoustic power requirements necessary for pasteurization could be greatly reduced by carrying the process out under pressures reduced below atmospheric pressure. The acoustic power which must be generated by an acoustic transducer is a function of the square of the applied static pressure. Therefore it is possible to greatly reduce the required power by reducing the static pressure.

A further limitation of the prior art was the failure to recognize that degassing, could be greatly accelerated by varying or modulating the frequency of the compressional waves so that the frequency was maintained at or very near the resonant frequency of the bubbles produced during the process of degasification. Although it was known that compressional waves at or near the resonant frequency of a bubble lead to greater bubble growth rates. No one has heretofore recognized that varying the frequency to constantly coincide with the natural frequency of the bubble will greatly accelerate the growth rate. This invention also recognizes that power requirements can be reduced by modulating the instantaneous frequency of the compression waves to match the instantaneous frequency which is most effective at degassing or microorganism disintegration.

The converse of bubble growth is dissolving bubbles into a liquid or gasification. The concept of this invention to vary compressional wave frequency for maximizing the degassing rate also applies conversely to bubble diffusion and gasification so that greatly improved rates of gasification can be obtained using this method.

Other advantages and objectives of the invention will be apparent from the following detailed description.

BRIEF DESCRIPTION OF THE DRAWINGS

A preferred embodiment of this invention is illustrated in the accompanying drawings, in which:

FIG. 2 is an enlarged isometric view of the pasteurization subsystem including the degasifier, microorganism disintegrator, and interstage pump shown in FIG. 1;

FIG. 3 is an enlarged side sectional view of the regasification subsystem shown in FIG. 1;

DETAILED DESCRIPTION OF THE PREFERRED EMBODIMENTS

Figure 1:
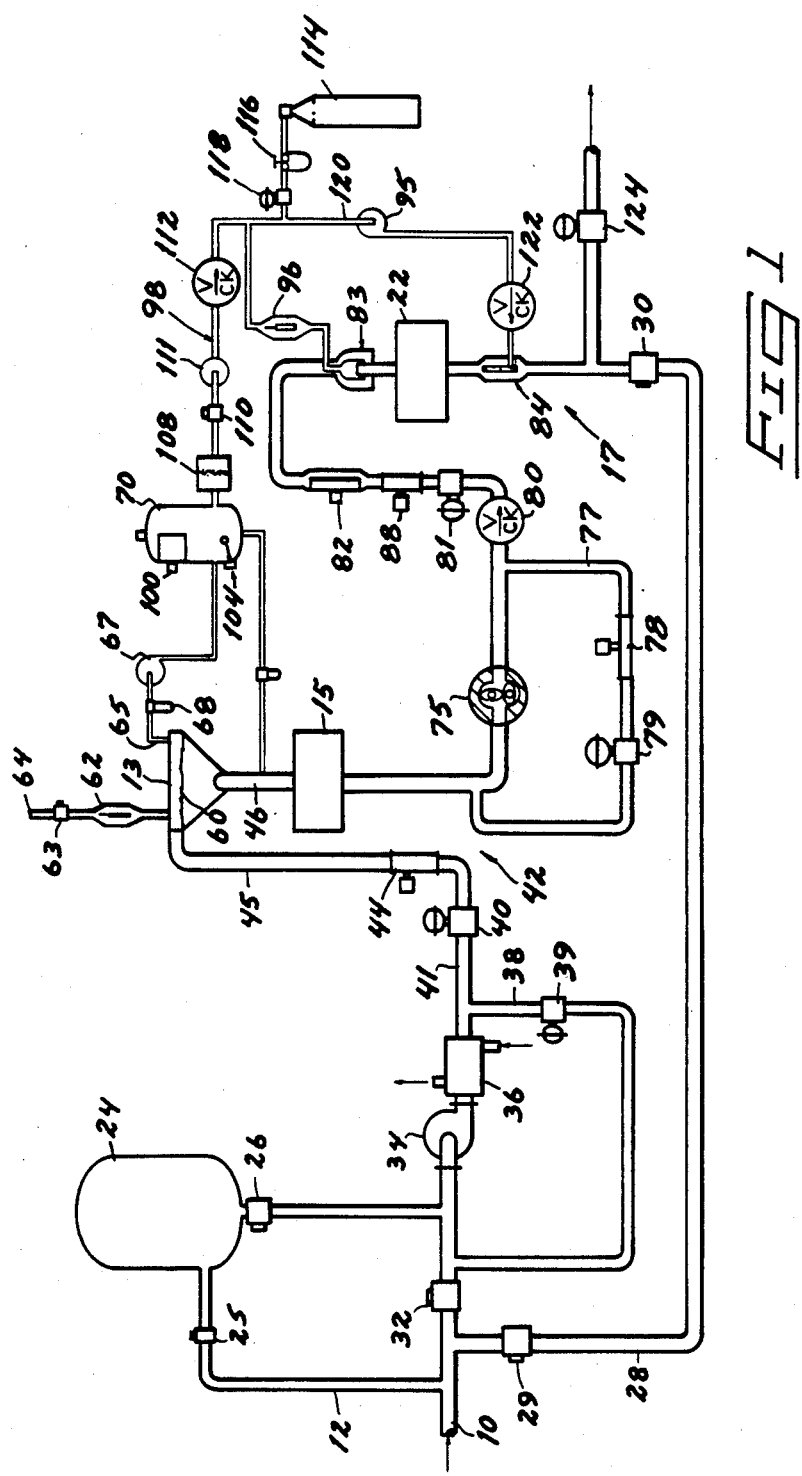
FIG. 1 is a schematic representation of the regasifying pasteurization system of this invention.

In compliance with the constitutional purpose of the Patent Laws "to promote the progress of science and useful arts" (Article 1, Section 8), applicant submits the following disclosure of the invention.

The invention includes a system for pasteurizing liquids without heat using compression waves. The system can be used to pasteurize milk, water, beer, soft drinks, fruit juices and other liquids commonly containing microorganisms which must be killed so that the liquids can be stored for relatively long periods of time.

The pasteurization system is advantageously combined with a regasification system which injects gases removed during pasteurization back into the liquid. The regasification system is combined with the pasteurization system to produce the regasifying pasteurization system of this invention. The regasification system is particularly important in cases such as beer and other liquids which contain dissolved gases which are preferably kept in the liquid for taste or other reasons. The regasification system can also be used to initially gasify a liquid.

The invention also includes a degasification method and apparatus which forms a part of the pasteurization system discussed above, and a method for disintegrating microorganisms.

The general method or process of the regasifying pasteurization system is to first remove approximately all of the dissolved gases from the liquid in a process called degasification. Degasification is performed in a compressional wave degasifier 13 (FIG. 1) or similar degasification unit under pressures reduced below atmospheric pressure. Degasifier 13 generates compressional waves in the liquid which greatly increase the speed at which degassing occurs.

After degassing, the liquid being processed proceeds into a compressional wave microorganism disintegrator 15. The disintegrator uses varying or modulated frequencies of vaporously cavitating compressional waves to break up microorganisms and kill them. The disintegration step also is performed under static pressures reduced below atmospheric pressure to greatly reduce the acoustic power necessary to kill the microorganisms. Alternatively, there may be circumstances where it is desirable to perform the disintegration step under increased pressure rather than the reduced pressures of less than atmospheric.

Liquid coming from disintegrator 15 is pasteurized and ready for use or further processing. In the case of beer or other liquids which need to be regasified, the liquid is pressurized and pumped to a regasification subsystem 17. The regasification subsystem preferably uses the gases removed from the beer or other liquid during degasification, and injects these gases back into the liquid in the form of tiny bubbles using bubble generator 20. The bubles are then dissolved into the liquid by regasifier 22 using compression waves. The liquid flowing from regasification subsystem 17 is both pasteurized and regasified and ready to package, bottle or process further.

Having briefly outlined the regasifying pasteurization system, it will now be more fully described with reference to the various components shown in FIG. 1. Liquid being processed flows in through inlet piping 10. Branch line 12 extends up to a chlorinated water wash tank 24 which is isolated by solenoid controlled valves 25 and 26. Highly chlorinated water contained in wash tank 24 is circulated through the regasifying pasteurization system to fully clean the system. Branch line 28 is used to recycle the chlorinated wash water from the outlet of the regasification subsystem 17 back for storage in tank 24. Valves 29 and 30 allow for isolation of branch line 28.

Incoming liquid passes through a main entry valve 32. Infeed pump 34 receives liquid from valve 32 and pressurizes the liquid for flow through viscosity heat exchanger 36. Viscosity heat exchanger 36 does not serve to heat the liquid for pasteurization purposes but instead is used to either heat or cool the incoming liquid to a desired temperature to regulate the viscosity of the liquid.

A recirculation line 38 is preferably provided downstream of infeed pump 34. Recirculation line 38 is provided with a servo controlled valve 39 which is automatically controlled in conjunction with servo controlled valve 40 which is in the main liquid flow line 41. Servo controlled valve 40 throttles the pressure and adjusts the quantity of liquid allowed to enter into the reduced pressure of pasteurization subsystem 42. A flowmeter 44 is preferably provided downstream of control valve 40 for better control of the process.

Liquid flowing through control valve 40 passes through line 45 and into the degasifier 13. Degasifier 13 is more clearly shown in FIG. 2. FIG. 2 shows that degasifier 13 has two angled sidewalls 51 and 52 which form a trough like shape. End walls 53 and 54 are securely connected to side walls 51 and 52 at each end. A top 55 is connected to sidewalls 51 and 52 and end walls 53 and 54 to form an enclosed interior space 56. Incoming liquid flows in through inlet 57 and outflowing liquid flows through outlet 58.

Degasifier 13 also includes a plurality of compressional wave transducers 59 placed along sidewalls 51 and 52 in a spaced array. The sidewalls are vibrated by transducers 59 to create compressional waves in liquid contained in degasifier 13. The sidewalls 51, 52 are ideally oriented in a diverging configuration toward the top so that each sidewall forms an angle of approximately 45° from vertical. In this arrangement the sidewalls 51 and 52 are symmetrically spaced from the liquid level 60 (FIG. 1) in the degasifier. The distance between the resonating sidewalls 51, 52 and the level of liquid 60 also varies continuously between the top and bottom of the sidewalls, as measured along lines perpendicular to sidewalls 51 and 52. This arrangement allows better resonation of the liquid over a wide range of compressional wave frequencies.

Degasifier 13 is also preferably provided with a purge port 61 and air release valve 62 for purging degasifier 13 of air during startup of the process. A solenoid controlled valve 63 is used to close purge line 64 during normal operation.

Degasifier 13 is further provided with a vacuum port 65 for taking away gases released from the liquid by the action of the degasifier. A vacuum pump 67 (FIG. 1) or other vacuum producing vacuum pump means is used to reduce the static degassing pressure in degasifier 13 to below atmospheric pressure. A gas-liquid separator 68 can advantageously be employed upstream of vacuum pump 67 to prevent injury to the vacuum pump when liquid condenses or is accidentally drawn through port 65. Vacuum pump 67 also pressurizes the gases removed from the liquid, and sends them to degas tank 70 which will be discussed more fully below.

The preferred method of degassing or degasifying liquids according to this invention will now be described. This degasification method first involves subjecting the liquid to a degasification static pressure which is below atmospheric pressure and above the vapor pressure of the liquid in its then-existing state. The static degasification pressure being preferably slightly greater than the vapor pressure of the liquid to prevent excessive boiling of the liquid. The low static pressure also reduces the acoustic power required to create compressional waves in the liquid. In the case of water at 50° F. the vapor pressure is approximately 29.5 inches of Hg vacuum. Static pressures in the range 29.5 to 25.5 inches of Hg vacuum are considered slightly above the vapor pressure of the water in its then-existing state.

The next step of the method for degassing is creating compressional waves within the liquid. The compressional waves are preferably varied with time in a reoccurring cyclical frequency sweep pattern. This degassing frequency sweep pattern preferably starts at a relatively high frequency and changes to a relatively low frequency. A range of possible frequencies is 600 kilohertz ($KH_Z$) to 8 $KH_Z$. The rate of change of the degassing frequency sweep pattern is preferably designed to match or coincide with the change in the natural frequency of bubbles growing within the liquid due to rectified diffusion caused by the compressional waves. This method for growing bubbles and degassing minimizes the time necessary to remove gases dissolved in the liquid by maximizing the growth rate of gas bubbles. When the gas bubbles have grown sufficiently large, they then float up through the liquid and are drawn off by vacuum pump 67.

Although there are an indefinite number of possible degassing frequency sweep patterns one mathematical model has been developed for solving the problem of matching the frequency of the degasifier with the natural frequency of the growing bubbles to achieve a maximum bubble growth rate. Theoretically the maximized bubble growth rate will correspond to a minimum time required for degassing the entire liquid. The mathematical model used will now be explained to enable those of ordinary skill in the art to practice the preferred form of this invention.

Rectified diffusion is a term identifying the growth of bubbles in a liquid subjected to an acoustic or compressional wave field of sufficient acoustic pressure amplitude. A bubble undergoing rectified diffusion grows at a rate described by the differential equation $$\frac{dR}{dt} = \frac{Dd_1}{R}\left[\frac{Ri}{R}\right]\left(1 + \frac{4s}{3P \cdot R}\right)^{-1} \times H$$

wherein $$H = \frac{C_i}{C_o} - \left(1 + \frac{2S}{R \cdot P}\right)\frac{\left[\frac{R_i}{R}\right]}{\left[\frac{R_i}{R}\right]^4}$$

$$d_1 = (B \cdot T \cdot C_o)/P$$

with
R = radius of bubble at rest or in equilibrium
$R_i$ = instantaneous radius of bubble in acoustic field
B = universal gas constant
D = diffusion constant
T = absolute temperature
$C_o$ = saturation gas concentration
$C_i$ = average gas concentration far from bubble
S = surface tension at gas-liquid interface
P = static pressure in liquid near bubble The brackets, [ ], are used to indicate the time average over one or two oscillations of the quantity contained therewithin.

The factors [Ri/R] and [(Ri/R)⁴] are key factors which reflect the short term conditions of the bubble as it oscillates in response to the acoustic field. The instantaneous radius of a bubble in a sound field has been described by the equation:

$$R_i \frac{d^2R_i}{d+2} + \frac{3}{2} \frac{(dR_i)^2}{dt} +$$

$$\frac{1}{P}\left(\frac{2s}{R_i} - \left(P + \frac{2s}{R}\right)\left(\frac{R}{R_i}\right)^3 + P + Pa \cos Wt\right) +$$

$$\frac{RW_o}{Q} \times \frac{dR}{dt} = 0$$

with the symbols used above and with the following new symbols
W = angular frequency of the acoustic field
Wo = angular frequency of the resonate bubble
t = time
Q = qualify factor (which will be described below)
Pa = acoustic pressure amplitude Due to the complexity of this equation, an approximate analytical solution was derived using a second order perturbation approach. The approximate solution is expressed as an expansion in Pa/P; and is as follows:

$$R_i/R = 1 - (Pa/p) \cos Wt + A^2 L(Pa/P)^2$$

$$A^{-1} = (p\ R^2/P)\ ((W_o^2 - W)^2 + (W \cdot W_o/Q)^2)^{\frac{1}{2}}$$

$$L = \frac{1 - p\ W^2R^2/12P + 5s/3PR}{(1 + 4s/3PR)}$$

The time averages over relatively short periods of oscillations, such as 1–2 oscillations, was expressed as the following from the above equations:

$$[R_i/R] = 1 + A^2L(Pa/P)^2$$

$$[(R_i/R)^4] = 1 + (3 + 4L)A^2(Pa/Po)^2$$

The computation of the quality factor Q is complicated and is fully developed in an article by Andrea Prosperetti, *Journal of Acoustical Society of America*, Vol. 57, No. 4, April 1975 p. 810.

Also relevant to the model is the empirical equation describing the natural frequency of a bubble. The natural frequency represents the frequency at which the bubble oscillates with the greatest relative amplitude with the least amount of acoustic pressure amplitude, and is represented by the following equation:

$$W_o = \left(\frac{3P}{pR^2}\left(1 + \frac{4s}{3 \cdot P \cdot R}\right)\right)^{\frac{1}{2}}$$

where Wo is the angular frequency at resonance in radians/sec and is converted into Hertz (cycles per second) by dividing by $2\pi$.

The acoustical pressure threshold must also be taken into account in the model since growth by rectified diffusion takes place only when the acoustic pressure is greater than the threshold. The threshold varies as a function of bubble size and frequency. The lowest threshold values being associated with the natural frequency of the bubble. For the purpose of generating data from this model, the acoustic pressure Pa was assumed to be some value. The model is then calculated preferably using a computer and the data is then considered. Adjustment of the acoustic pressure amplitude is made if necessary.

The average gas concentration far from the bubble, $C_i$, also varies because the dissolved gas concentration decreases as bubbles grow. The rate of change in average dissolved gas concentration is described by the following differential equation which is the rate of desaturation of the liquid:

$$\frac{dC_i}{dt} = -C_b\left(4\pi DR\left[\frac{R_i}{R_o}\right]C_oH\right)$$

where
n = number of kilomoles of gas in one bubble
$C_b$ = number of bubbles per unit of volume The equations for rate of change in bubble radius and rate of change in average gas concentration result in a system of two highly non-linear first order differential equations which are solved simultaneously to derive an expression for frequency as a function of time. The differential equations are:

$$\frac{Dd}{R}[R_i/R]\left(1 + \frac{4s}{3P \cdot R}\right)^{-1}\left(\frac{C_i}{C_o} - \left(1 + \right.\right.$$

$$\left.\left.\frac{2s}{P \cdot R}\right)\frac{[R_i/R]}{[R_i/R]^4}\right) - \frac{dR}{dt} = 0$$

and $$4\pi \cdot C_o \cdot D \cdot R \cdot C_o[R_i/R]C_i/C_o - \left(1 + \right.$$

$$\left.\frac{2s}{P \cdot R}\right)\frac{[R_i/R]}{[R_i/R]^4}\right) + \frac{dC_i}{dt} = 0$$

Initial conditions for $C_i$ can be estimated as the saturation concentration less the total amount of gas in bubbles and is represented by the following equation:

$$C_i = C_o - nNaC_b$$

Figure 4:
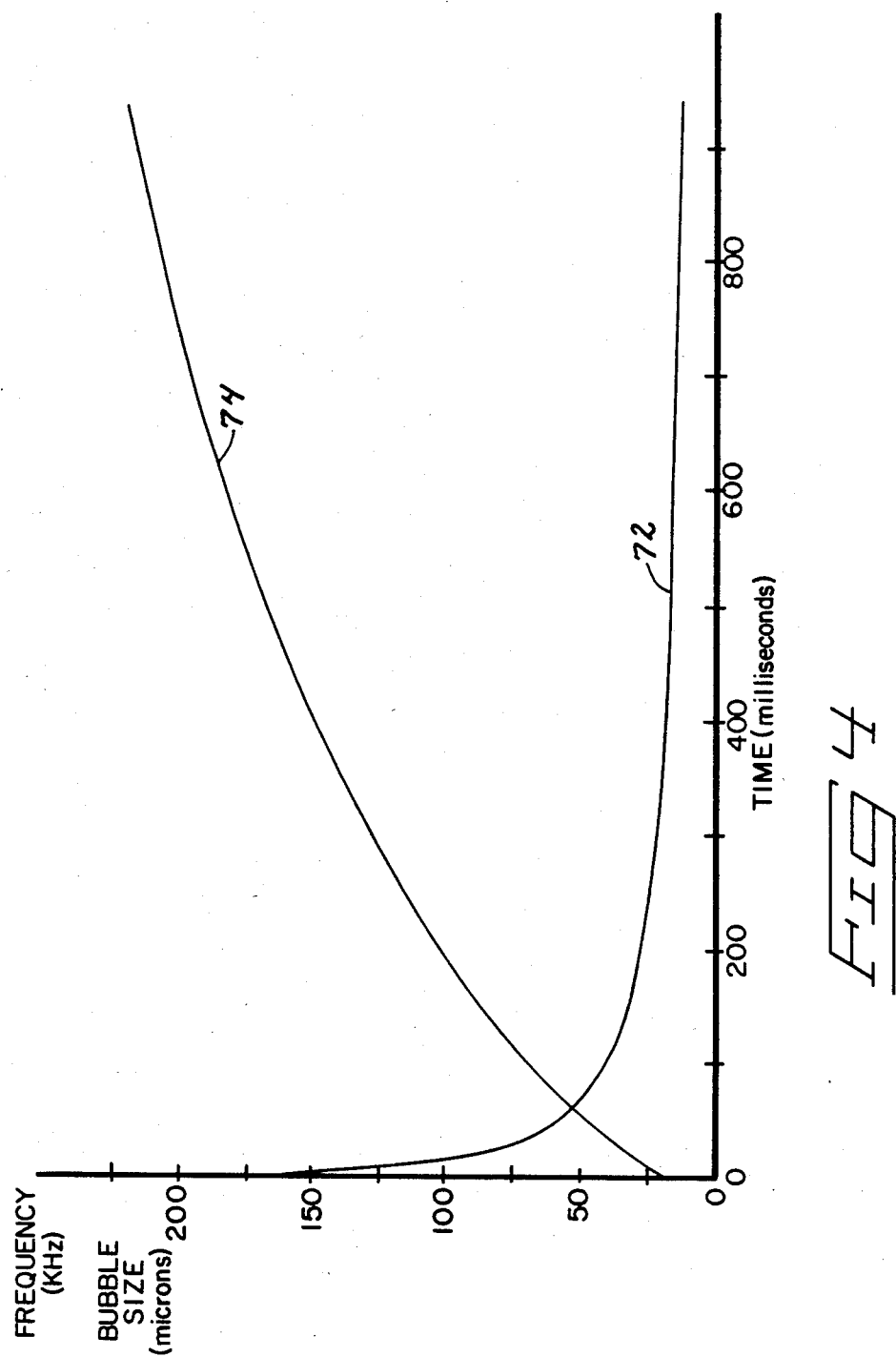
FIG. 4 is a graph showing one degassing frequency sweep pattern and the anticipated bubble radius size, both predicted by a mathematical model.

This system of differential equations is then solved to obtain an estimate of the rate of change in both natural frequency and the compressional wave frequency which is preferable for maximum bubble growth rate. An example of the resulting function is shown in FIG. 4 for frequency in kilohertz versus time 72 and for bubble radius in microns versus time 74.

The parameters used to produce FIG. 4 were as follows:

Operating Conditions static pressure P = 1.01 × 10⁵ newtons/square meter
acoustic pressure amplitude = 2.03 × 10⁴ newtons/square meter
temperature of liquid = 20° C.
density of liquid, p = 998 kilograms/cubic meter
liquid viscosity = 1.0 × 10⁻³ newton-seconds/square meter
surface tensions = 7.28 × 10⁻² newton/meter specific heat of liquid = $4.18 \times 10^3$ joules/kilogram °C.

thermal conductivity of liquid = $5.97 \times 10^{-1}$ kilograms/kilomole molecular weight of gas = $2.90 \times 10^{-1}$ kilograms/kilomole specific heat of gas = $1.00 \times 10^3$ joule/kilogram °C.

ratio of specific heats of gas = 1.40 thermal conductivity of gas = $2.57 \times 10^{-2}$ newton/second °C.

diffusion constant of gas in liquid, D = $2.0 \times 10^{-9}$ square meters/second saturation concentration of gas = $8.34 \times 10^{-4}$ kilomole/cubic meter speed of sound in liquid = $1.51 \times 10^3$ meters/second Initial Conditions initial bubble concentration, $C_i$ = $1.78 \times 10^8$ bubbles/cubic meter starting resonant frequency = 200 kilohertz time step size = 2 seconds maximum time to advance solution = $1.0 \times 10^3$ seconds final bubble radius desired = $4.0 \times 10^2$ micrometers or microns This mathematical model was carried out on a computer program which forms a part of this specification under the subsection entitled "Computer Program for Mathematical Bubble Growth Rate Model", which is included below.

Figure 5:
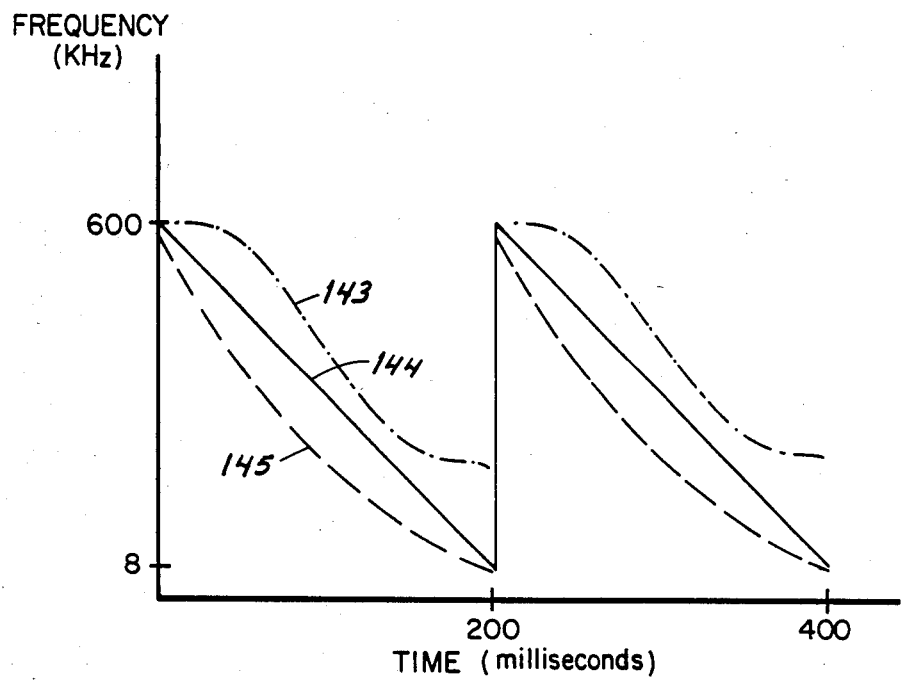
FIG. 5 is a graph showing several possible degasification and frequency sweep patterns.

The above development of the model is purely for illustrative purposes since many factors may actually change the maximum growth rate which is experienced under read conditions. No limitation should be placed on the degassing frequency sweep pattern generated by this theoretical model, but the model and FIG. 4 are illustrative of one degassing frequency sweep pattern 72 for air dissolved in water. The degassing frequency sweep patterns are repeated as necessary to fully degas the liquid. FIG. 5 also shows three alternative frequency sweep patterns 143–145.

Having described the degasification apparatus and method it is now appropriate to consider the method and apparatus for disintegrating microorganisms. The disintegration of microorganisms using compressional waves depends upon the frequency of the compressional waves and the acoustic pressure amplitude. The mechanism involved appears to be that of cavitational vapor bubbles imploding very rapidly in the space adjacent to a microorganism. This implosion breaks or tears away part of the microorganism if the size of the imploding vapor bubble and the microorganism are properly related. It appears that bubbles approximately the same size as the microorganism produce sufficiently violent forces on the microorganisms to kill them. Other sizes of imploding bubbles may also sometimes do damage but high acoustic power levels are required because the acoustic forces are not being most effectively converted into killing action.

The disintegration method of this invention preferably includes a variation or modulation in the disintegration or disintegrator frequency so that a wide variety of microorganisms are killed as efficiently as possible. Since the general purpose of the disintegrator 15 is to break up and kill the microorganisms, it is preferable to vary or modulate the frequency of the disintegration compressional waves from a relatively low frequency to a relatively high frequency. Such disintegration frequency sweep patterns produce larger cavitation bubbles when the frequency is low, thereby efficiently breaking up clumps of bacteria and large microorganisms. As the disintegration frequency increases, smaller cavitation bubbles are produced thereby progressively breaking up the clumps and microorganisms into smaller and smaller pieces.

Figure 6:
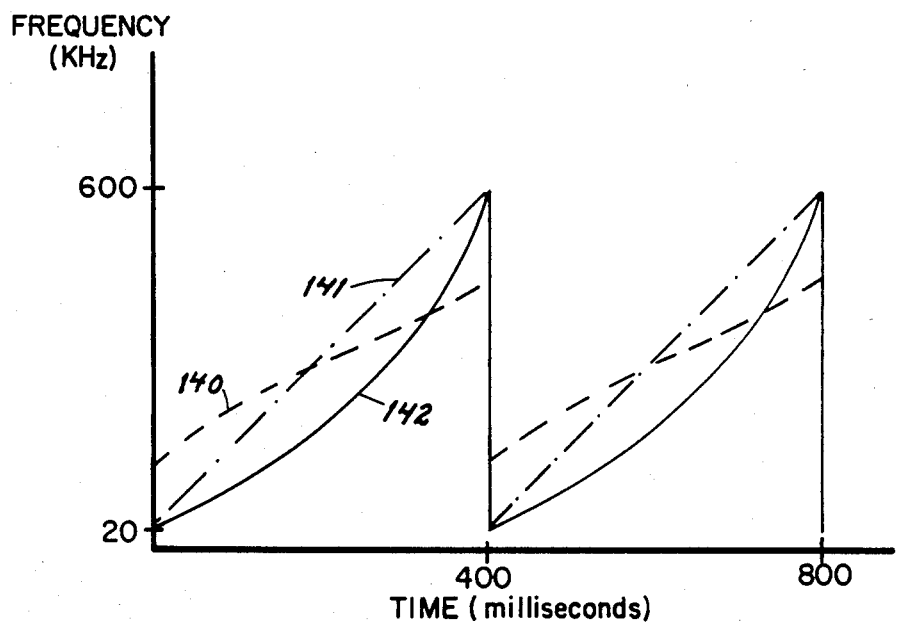
FIG. 6 is a graph showing several possible disintegration and regasification frequency sweep patterns.

The exact shape of the disintegrator frequency sweep pattern can be linear with time or can be some other shape which proves to be particularly advantageous. FIG. 6 shows three possible disintegration frequency sweep patterns 140, 141 and 142. It may also prove to be effective in some cases to modulate the frequency from high to low and this invention fully anticipates such a disintegrator frequency sweep pattern. A possible range of disintegration frequencies is between 20 KHz to 600 KHz as shown in FIG. 6. Many others are also possible, the specific requirements varying from liquid to liquid and due to special considerations such as the type of contamination and the like.

Continuous frequency variation or modulation is preferred under these methods but it is difficult to resonate the transducers and resonators along a truly continuously varying frequency sweep patterns for degasifier 13 disintegrator 15 and regasifier 22. Instead small incremental changes can be made in the frequency thereby producing small steps of frequency change. It is desirable to produce approximately ten cycles or more at one frequency step before proceeding to the next frequency step. The frequency sweep patterns are adjusted with regard to either the number of cycles at each frequency step, the amount of frequency increase from step to step, or both to generate the shape of curves 72, 140–145 shown in FIGS. 4–6. The frequency sweep patterns are repeated as necessary to perform the respective functions.

A preferred form of disintegrator 15 is shown in FIG. 2 connected to degasifier 13 by line 46. Disintegrator 15 can be any type of acoustic resonator which produces compressional waves within liquid over the range of frequencies neeeded. Disintegrator 15 preferably has four banks of acoustic transducers 126 arranged around the central reservoir 127 which holds liquid. An exterior wall supports the outer ends of transducers 126 but it has been removed to more clearly show the arrangement of disintegrator 15, and is suggested by the hidden lines 128.

The disintegrator 15 produces acoustical pressure amplitudes in the range of 0.3 barr or higher, as used in most cases. These relatively low levels of acoustic pressure must be compared with the prior art references which suggest pressure amplitudes of hundreds or thousands of barr as necessary for destruction of microorganisms. The ability to use lower levels of acoustic pressure reduces the acoustic power requirements and associated equipment.

Liquid treated by the pasteurization subsystem 42 should in most cases be free of all forms of microorganisms including bacteria and viral spores which are most resistant to attempts to kill them. The liquid can be used directly after pasteurization or can be further treated in any number of ways, including the regasification subsystem shown in FIGS. 1 and 3, which will now be more fully described.

FIGS. 1 and 2 show that after pasteurization in degasifier 13 and disintegrator 15 the liquid is pressurized and pumped by interstage pump 75. Interstage pump 75 is preferably a rotating two lobe type pump or some other positive displacement type pump requiring very little inlet pressure. The reduced or vacuum pressures under which degasifier 13 and disintegrator 15 operate make pump cavitation a particular problem. The two lobe pump has been chosen to help alleviate this problem although other types may be acceptable. It is also desirable to increase the interstage pump inlet head by positioning pump 75 beneath disintegrator 15 at least several feet to gain hydrostatic head. Placing pump 75 at even lower relative elevations will increase the available hydrostatic head thereby reducing the potential for cavitation of pump 75. The pump 75 can alternatively be placed between the degasifier 13 and disintegrator 15 where the disintegration is to be performed under increased pressure rather than reduced pressure.

A control loop 77 is preferably included from the outlet side to the inlet side of pump 75. This allows the flow of liquid through the pasteurization subsystem 42 to be interrupted or cycled in a semi-batch type flow scheme without loosing control of pump 75 or causing damage to the system. Flowmeter 78 and servo controlled valve 79 monitor and control flow through loop 77.

The main flow through the regasified pasteurization system proceeds from interstage pump 75 through check valve 80, servo controlled valve 81 and flow meter 88. An ultraviolet irradiator 82 or other interstage irradiation means can advantageously be placed at this point in the system to kill any surviving viral spores or other microorganisms. Interstage irradiator 82 is effective in situations where the liquid is transparent to the wavelength of ultraviolet light being used.

The output pressure of interstage pump 75 is preferably in the range from approximately atmospheric pressure to 120 pounds per square inch gauge. This range of pressures allows for easy regasification of beer, water, fruit juices and other similar liquids. Other operating pressures are also possible if the liquid and gases involved are more easily gasified or otherwise processed at higher or lower pressures.

The preferred regasification subsystem 17 of this invention will now be more fully described as shown in FIGS. 1 and 3. The regasification system includes a bubble trap 83, regasifier 22 and bubble generator 84. Microscopic bubbles are generated by bubble generator 84 in the liquid being processed. The bubbles produced by bubble generator 84 are preferably very small to reduce the acoustic power necessary to dissolve them into the liquid. Bubble generator 84 preferably includes a microporous stainless steel tube 85 having a large number of small holes, the size of the holes being on the order of 5 microns in diameter. Tube 85 is approximately concentrically located in a case 86 which provides an enlarged cross-sectional flow area through which the liquid flows about tube 85. Bubbles emanate from microporous tube 85 and float upwardly and into regasifier 22, countercurrent to the flow of liquid.

Regasifier 22 has a plurality of acoustic transducers 129 (FIG. 3) to vibrate surfaces of interior reservoir 130 which contains the liquid being processed. The compressional waves generated by the regasifier are preferably of a lower acoustic pressure amplitude than the threshold for growth through rectified diffusion. This assures that the bubbles will diminish in size rather than grow, as is known in the art. The compressional waves cause the small bubbles generated by the bubble generator to be rapidly diffused into the liquid to achieve an unsaturated, saturated or supersaturated gas solution in the liquid, as desired.

Regasifier 22 can also have a varying or modulated acoustic frequency to more effectively dissolve the bubbles into the liquid. The frequency modulation will preferably start at a relatively low frequency and increase to a relatively high frequency such as shown in FIG. 6. Such regasification frequency sweep patterns tend to break the bubbles up and dissolve them at a rapid rate. Mathematical models similar to that described above can also be developed and applied to determine the maximum rate of diffusion or dissolution of the gas bubbles into the liquid.

The regasification subsystem 17 is also provided with a bubble trap 83 for capturing excess bubbles which float up through and past the regasifier 22. The bubble trap is preferably constructed of three coaxial pipes. The outmost pipe forms an exterior casing 89 which also acts as a conduit for the liquid. Intermediate bubble cap 90 extends down and over the top edge of an inner pipe 91 which forms the exit conduit. Bubbles rise through inner pipe 91 and are trapped by bubble cap 90. The bubbles trapped in bubble cap 90 are drawn away by regasifier compressor 95 through an air release valve 96 which prevents liquid from passing therethrough.

The gases dissolved into the liquid by regasification subsystem 17 are preferably the same gases removed in the degasification step by degasifier 13. Using the gases removed from the liquid insures that the same taste and basic constituents remain in the liquid after pasteurization as existed before.

In order to assure pasteurization of the final liquid product, it is necessary that the gases recycled from the degasifier be pasteurized before injecting them into the pasteurized liquid. To do this the recycle gas line 98 is provided with a degas tank 70 which receives gas at approximately atmospheric pressure from vacuum pump 67. The degas tank 70 is preferably provided with at least one ultraviolet irradiator 100 or other irradiation means which irradiates microorganisms and kills them according to well known technology.

Degas tank 70 is preferably provided with a drain line 102 which takes condensed liquid from the degas tank and injects it back into the main liquid process line 46 between the degasifier 13 and disintegrator 15. The degas tank is also preferably provided with a float switch 104 which controls solenoid valve 106 thereby allowing condensed liquid in the degas tank to flow back into the main liquid line, but only when necessary. This arrangement assures that gas is not injected into the main liquid stream after it has been degassed in degasifier 13.

Gases held in degas tank 70 proceed from the tank through recycle gas line 98 and through an ultrafine filter 108 or other ultrafine filtration means for removing live or dead microorganisms which may still be in the gases. Solenoid controlled valve 110 is used to open or close the flow of recycle gas. Compressor 111 draws gases from degas tank 70 and pressurizes them as needed for use in the regasification subsystem 17. A check valve 112 is preferably provided downstream of compressor 111.

Recycle gases from degas tank 70 may not be sufficient at all times to adequately supply the regasification system's entire need. To supplement the regasification system there is a bottle of compressed gas 114. Compressed gas from bottle 114 feeds through a pressure regulator 116. Servo controlled valve 118 is used to accurately control the pressure at which bottled compressed gas is fed into the regasification system. Bottled gas is advantageously provided at 2 pounds per square inch lower pressure than the usual pressure in line 120.

Recycled or bottled gas flowing through line 120 is pressurized by regasifier compressor 95 to the desired injection pressure. The injection pressure must be greater than the liquid pressure in the regasification system so that the gases will be injected and bubbled. A check valve 122 is advantageously provided between the outlet of regasifier compressor 95 and the bubble generator 84. The completed regasified and pasteurized liquid flows out of the system through servo control valve 124 and on to bottling or other processing.

The regasification or gasification method of this invention is performed by the process equipment just described or can be accomplished with substantially different equipment and without the counterflow arrangement. The method first includes the step of injecting small gas bubbles into a liquid under pressures greater than atmospheric pressure. Compressional waves are then created in the liquid injected with gas bubbles. The compressional waves cause the gas bubbles to be diffused into the liquid to create an unsaturated, saturated or supersaturated gas-liquid solution. The method also preferably includes the step of trapping excess undissolved gas bubbles and recirculating them for injection back into the liquid.

Although the processes, methods and systems described in this application are generally shown as continuous flow, it is readily apparent that all can be adapted and performed using batch processing. This invention fully contemplates such batch processing and the apparatuses used therein.

In compliance with the statute, the invention has been described in language more or less specific as to structural features. It is to be understood, however, that the invention is not limited to the specific features shown, since the means and construction herein disclosed comprise a preferred form of putting the invention into effect. The invention is, therefore, claimed in any of its forms or modifications within the proper scope of the appended claims, appropriately interpreted in accordance with the doctrine of equivalents.

I claim:

1. A method for treating liquids containing dissolved gases and microorganisms so that at least portions of the microorganisms are destroyed and at least portions of said dissolved gases are present in resulting treated liquid in order to maintain distinctive flavors associated therewith, comprising:
   degassing a liquid to remove approximately all of the dissolved gases by subjecting the liquid to a static degasification pressure which is below atmospheric pressure and above the vapor pressure of the liquid in its then-existing state, and by creating degassing compressional waves within the liquid to hasten removal of dissolved gases therefrom;
   disintegrating microorganisms contained in the liquid degassed in the previous step using vaporously cavitating compressional waves;
   pressurizing the liquid after the degassing step above;
   regasifying the liquid after the liquid has been subjected to said disintegrating step by injecting small bubbles of gas into the liquid, and creating compressional waves in the liquid injected with bubbles of gas at least a portion of which is gas previously dissolved within and removed from the liquid during the degassing step, to thereby dissolve the bubbles of gas into the liquid.

2. The method of claim 1 wherein pressurizing the liquid occurs after the disintegrating step.

3. The method of claim 1 wherein the bubbles of gas used to regasify the liquid are at least one half constituted from gases removed from the liquid in the degassing step.

4. The method of claim 3 wherein gases removed by the degassing step are irradiated to kill microorganisms contained therein prior to injecting the gases back into the liquid.

5. The method of claim 4 further comprising the step of filtering the irradiated gases prior to injecting the gases back into the liquid, to thereby remove microorganisms from the gases.

6. The method of claim 1 further comprising the step of irradiating the liquid between the steps of disintegrating and regasifying, to kill microorganisms contained therein.

7. The method of claim 1 wherein the step of disintegrating microorganisms occurs while subjecting the liquid to a static disintegration pressure which is below atmospheric pressure.

8. The method of claim 1 wherein static degasification and disintegration pressures are approximately equal.

9. The method of claim 1 wherein static degasification and disintegration pressures are slightly greater than the vapor pressure of the liquid.

10. The method of claim 1 wherein the method is applied in a continuous flow process.

11. The method of claim 1 wherein the method is applied in a batch process.

12. The method of claim 1 wherein said degassing compressional waves are provided at degassing frequencies which vary with time to increase the growth rate of gas bubbles within the liquid thereby causing the liquid to be degassed more quickly.

13. The method of claim 12 wherein the degassing compressional waves are provided at degassing frequencies which vary in a reoccurring degassing frequency sweep pattern; the degassing frequency sweep pattern starting at a relatively high frequency and decreasing to a relatively low frequency.

14. The method of claim 1 wherein the disintegration compressional waves are provided at disintegration frequencies which vary with time to vary the size of cavitational vapor bubbles produced and kill various sizes of microorganisms in a minimum amount of time.

15. The method of claim 14 wherein the disintegration compressional waves are provided at disintegration frequencies which vary in a reoccurring disintegration frequency sweep pattern; the disintegration frequency sweep pattern starting at a relatively low frequency and increasing to a relatively high frequency.

16. The method of claim 1 wherein the degassing compressional waves are provided at degassing frequencies which vary with time, and the disintegration compressional waves are provided at disintegration frequencies which also vary with time.

17. The method of claim 16 wherein the degassing frequencies vary in a reoccurring degassing frequency sweep pattern which starts at a relatively high frequency and decreases to a relatively low frequency; and the disintegration frequencies vary in a reoccurring disintegration frequency sweep pattern which starts at a relatively low frequency and increases to a relatively high frequency.

18. The method of claim 17 wherein the degassing frequencies vary within the range from approximately 600 KHz to 8 KHz and the disintegration frequencies vary within the range from approximately 20 KHz to 600 KHz.

19. The method of claim 18 wherein the degassing and disintegrating compressional waves are produced with acoustic pressure amplitudes which vary during the respective frequency sweep patterns to thereby minimize the acoustic power required.

* * * * *